United States Patent
Braun et al.

(10) Patent No.: US 6,720,465 B2
(45) Date of Patent: Apr. 13, 2004

(54) PREPARATION OF HIGHLY PURE FLUORINE COMPOUNDS

(75) Inventors: Max Braun, Wedemark (DE); Carsten Brosch, Hannover (DE); Heinz Gress, Hannover (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 284 days.

(21) Appl. No.: 10/086,636

(22) Filed: Mar. 4, 2002

(65) Prior Publication Data
US 2002/0157940 A1 Oct. 31, 2002

Related U.S. Application Data

(63) Continuation of application No. PCT/EP00/08313, filed on Aug. 25, 2000.

(30) Foreign Application Priority Data
Sep. 4, 1999 (DE) .......................... 199 42 305

(51) Int. Cl.[7] .......................... C07C 17/38; C07C 19/08
(52) U.S. Cl. ...................................... 570/177; 570/134
(58) Field of Search ................................. 570/177, 134

(56) References Cited

U.S. PATENT DOCUMENTS

| | | | |
|---|---|---|---|
| 3,218,363 A | | 11/1965 | Haszeldine et al. |
| 5,175,380 A | | 12/1992 | Raab |
| 5,240,574 A | | 8/1993 | Fub et al. |
| 5,326,918 A | | 7/1994 | Correia et al. |
| 5,336,377 A | * | 8/1994 | Yates et al. |
| 6,077,982 A | * | 6/2000 | Yates et al. |

FOREIGN PATENT DOCUMENTS

| | | |
|---|---|---|
| GB | 2318350 | 4/1988 |
| GB | 2272696 | 5/1994 |
| WO | WO 97/37955 | 10/1997 |

* cited by examiner

*Primary Examiner*—Alan Siegel
(74) *Attorney, Agent, or Firm*—Crowell & Moring LLP

(57) ABSTRACT

A process for preparing purified, saturated, partially fluorinated or perfluorinated hydrocarbon compounds from crude products which are contaminated with impurity compounds which absorb light at a wavelength of $\lambda > 200$ nm by irradiating the crude product with UV radiation of a wavelength of $\lambda > 200$ nm and thereafter recovering highly pure, partially fluorinated or perfluorinated hydrocarbon compounds from the irradiated reaction product, for example, by simple vacuum distillation.

11 Claims, No Drawings

PREPARATION OF HIGHLY PURE FLUORINE COMPOUNDS

CROSS REFERENCE TO RELATED APPLICATIONS

This application is a continuation of international patent application no. PCT/EP00/08313, filed Aug. 25, 2000, designating the United States of America, and published in German as WO 01/17933, the entire disclosure of which in incorporated herein by reference. Priority is claimed based on Federal Republic of Germany patent application no. DE 199 42 305.9, filed Sep. 4, 1999.

BACKGROUND OF THE INVENTION

The invention relates to a process for the preparation of purified, partially fluorinated and perfluorinated hydrocarbons. Partially fluorinated hydrocarbons may for example be used as blowing agents for the manufacture of foamed plastics or to produce medicinal aerosols. Perfluorocarbons are suitable, for example, as blood substitutes or in the manufacture of ultrasound contrast media.

Perfluorocarbons are prepared, for example, by reacting hydrocarbons or partially fluorinated hydrocarbons with elemental fluorine or fluorine-emitting, higher-valency metal fluorides. There are many processes for the preparation of partially fluorinated hydrocarbon compounds. These include, for example, the non-exhaustive fluorination of hydrocarbons with elemental fluorine or fluorine-emitting, higher-valency metal fluorides, (usually catalysed) chlorine-fluorine exchange in the liquid phase or the gas phase, the addition of hydrogen fluoride to unsaturated starting compounds, or a combination of several of these processes. The resulting crude products, due to the way in which they are prepared, are frequently contaminated by unsaturated hydrocarbons, by unsaturated hydrocarbons containing chlorine and/or fluorine, or by hydrocarbons substituted by chlorine and optionally fluorine. Separation by distillation is often difficult because the desired products form azeotropic or azeotrope-like mixtures with impurities. It is already known that such crude products may be purified by purifying the unsaturated compounds or the chlorine-containing impurities by means of sorbents such as activated carbon or silica gel or by reaction with reactants with hydrogen, elemental fluorine or chlorine.

U.S. Pat. No. 3,218,363 discloses the purification of perfluoro- and perfluorochlorocarbons with the aim of removing olefinic or hydrogen-containing impurities. To this end, the contaminated crude product is treated with a strong oxidising agent. In so doing, photochemical energy can be radiated in. WO 97/379 955 discloses a process for the removal of olefinic impurities from 1,1,1,3,3-pentafluoropropane by photochlorination. GB-A-2 318 350 discloses the removal of olefinic impurities from hydrochlorofluoroethanes by photochlorination.

SUMMARY OF THE INVENTION

It is an object of the present invention to provide an effective process for the purification of perfluorocarbons and fluorohydrocarbons.

Another object of the invention is to provide a purification process for perfluorocarbons or fluorohydrocarbons which is simple to perform.

These and other objects are achieved in accordance with the present invention by providing a process for the preparation of a saturated, purified, partially fluorinated or perfluorinated hydrocarbon with 1 to 10 carbon atoms from a crude product which is contaminated by at least one impurity which absorbs light having a wavelength of $\lambda > 200$ nm, the process comprising irradiating the crude product with UV radiation having a wavelength of $\lambda > 200$ nm, and recovering the purified partially fluorinated or perfluorinated hydrocarbon from the irradiated reaction product.

In accordance with a further aspect of the invention, the objects are achieved by providing a mixture of a partially fluorinated or perfluorinated hydrocarbon with 1 to 10 carbon atoms and at least one higher boiling chlorine-containing higher boiling compound, obtained by UV irradiation of a crude product which contains said partially fluorinated or perfluorinated hydrocarbon with 1 to 10 carbon atoms and at least one impurity which absorbs light at $\lambda > 200$ nm.

The invention is based on the discovery that irradiation of such crude products by means of light of a wavelength of $\lambda > 200$ nm permits purified perfluorocarbons or fluorohydrocarbons to be obtained. Without this explanation being interpreted as being restricting, as an explanation it is assumed that the perfluorocarbons or fluorohydrocarbons are not influenced by the light radiated in, whereas the impurities react by polymerisation, chlorine splitting and further reaction of the resulting radicals and any other reactions to form higher-boiling products, which can easily be separated from the perfluorocarbons or fluorohydrocarbons.

The process according to the invention for the preparation of purified saturated partially fluorinated and perfluorinated hydrocarbons with 1 to 10 carbon atoms from crude products which are contaminated by compounds which absorb light of a wavelength of $\lambda > 200$ nm, provides for the crude product to be irradiated with UV radiation of a wavelength of $\lambda > 200$ nm and for purified partially fluorinated or perfluorinated hydrocarbons to be recovered from the irradiated reaction product. Aliphatic and cycloaliphatic hydrocarbons may be purified.

Preferably the process is used to prepare purified partially fluorinated and perfluorinated hydrocarbons which are contaminated with alkenes and/or alkanes, which are substituted by chlorine and optionally fluorine. Partially fluorinated hydrocarbons have at least 1 fluorine atom and at least 1 hydrogen atom.

Irradiation is also possible with UV light which has a wavelength $\lambda$ below 200 nm, for example down to 180 nm. What is important is that the radiation source emits radiation in the absorption range of the impurities, usually between 200 and 250 nm. In this case, the emitted spectrum need not be continuous; individual wavelengths in the aforementioned range are sufficient.

The process according to the invention is suitable for the preparation of purified compounds, in particular also for the preparation of highly pure compounds. In this process, the term "purified" means that the resulting products are less contaminated with impurities than the crude product. The term "extremely pure" means that the resulting products have at most 5 ppm, preferably at most 1 ppm, of each impurity. The degree of purification is dependent on the duration of irradiation and the radiation output of the light source. The longer and more intensive the irradiation is, the purer a product can be obtained. The desired degree of purity can be checked by the conventional analyses, in particular gas chromatography-mass spectrometry (GC-MS).

The purified products can be separated from the irradiated mixture by simple distillation. The temperature advantageously lies in the range of −30° C. to +100° C., because it is at that point that the impurities usually boil. Preferably one operates at 0 to 30° C. However, if desired the operating temperature may also lie in a higher or lower range. Preferably irradiation takes place in the liquid phase, although irradiation may also take place in the gas phase.

Particularly preferably, the process according to the invention is suitable for the preparation of partially fluorinated or perfluorinated C1–C5-alkanes (also cycloalkanes), in particular of purified or highly pure difluoromethane, 1,1,1,2-tetrafluoroethane, pentafluoroethane, pentafluoropropane, preferably HFC-245 fa; hexafluoropropane, pentafluorobutane, preferably HFC-365 mfc, perfluoropropane or perfluorobutane.

The irradiation can, for example, be performed in quartz vessels. A highly suitable product is e.g. Suprasil™, manufactured by Heraeus. Of course other materials which are permeable in the required range can also be used. The lamp advantageously may be cooled with compressed air in order to avoid light absorption by cooling water (which may be partially contaminated).

If desired it is also possible in a first step to convert the unsaturated impurities into chlorine-containing products by chlorination (e.g. photochlorination) and then, without addition of reactants, to perform the irradiation according to the invention.

With the process according to the invention, it is possible to purify fluorohydrocarbons and/or perfluorocarbons in a simple manner. With a sufficiently long duration of irradiation, it is possible to obtain highly pure products, which for example can be used in pharmaceutical applications or in the electronics industry.

The invention also relates to an irradiated mixture comprising partially fluorinated or perfluorinated hydrocarbons with 1 to 10 carbon atoms and the higher boilers formed upon irradiation, which have been formed upon the irradiation from chlorinated alkenes or chlorinated alkanes.

The following examples are intended to explain the invention further, without limiting its scope.

EXAMPLE 1

Preparation of Purified 1,1,1,3,3-pentafluorobutane

The crude product contains olefinic $C_4ClF_3H_4$ isomers as the main impurity.

Apparatus 365 mfc was placed in a 1.5 liter immersed-shaft photochemical reactor equipped with a mercury radiator TQ 150 from Heraeus Noblelight and was irradiated through quartz glass at room temperature. The lamp was cooled with compressed air in order to avoid any absorption of light by cooling water.

The 365 mfc contained the following impurities before the experiment began:

| | |
|---|---|
| 3610 ppm | $C_4ClF_3H_4$(2 olefinic isomers) |
| 80 ppm | $CCl_4$ |
| 40 ppm | $ClFC=CCl_2$(1111) |
| 128 ppm | $Cl_2C=CCl_2$(PCE) |
| 1000 ppm | $CCl_3F$(11) |

Further impurities which were present in amounts which were not quantified included: $CHCl_3$, $C_4H_5F_4Cl$, $C_4H_4F_3Cl$, $C_4H_5F_3Cl_2$, and $CH_3CFCl_2$.

After 180 minutes' irradiation, the experiment was interrupted. the long-chain compounds produced by photolysis could then be separated off by distillation and yielded a 365 mfc with 840 ppm $C_4ClF_3H_4$ and 37 ppm $CCl_4$. The other impurities could no longer be detected.

EXAMPLE 2

Purification of 1,1,1,3,3-pentafluorobutane Containing $CCl_4$ as the Principal Impurity 365 mfc was placed in a 1.5 liter immersed-shaft photochemical reactor equipped with a mercury radiator TQ 150 from Heraeus Noblelight and was irradiated through quartz glass at room temperature. The 365 mfc contained the following impurities before the experiment began:

| | |
|---|---|
| 20 ppm | $C_4ClF_3H_4$(2 olefinic isomers) |
| 80 ppm | $CCl_4$ |
| 5 ppm | $CHCl_3$ |
| 15 ppm | $ClF=Cl_2$(CFC-1111) |
| 25 ppm | $CCl_3F$(CFC-11) |

Further impurities which were present in amounts which were not quantified included: $C_4H_5F_4Cl$, $C_4H_4F_3Cl$, $C_4H_5F_3Cl_2$, and $CH_3CFCl_2$.

After 180 minutes' irradiation, the experiment was interrupted. The long-chain compounds produced by photolysis could then be separated off by distillation and yielded a 365 mfc with 3 ppm $CCl_4$ and 1 ppm $CHCl_3$. The other impurities could no longer be detected.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A process for the preparation of a saturated, purified, partially fluorinated or perfluorinated hydrocarbon with 1 to 10 carbon atoms from a crude product which is contaminated by at least one impurity which absorbs light having a wavelength of $\lambda > 200$ nm, said process comprising irradiating the crude product without addition of reactants with UV radiation having a wavelength of $\lambda > 200$ nm, and recovering the purified partially fluorinated or perfluorinated hydrocarbon from the irradiated reaction product.

2. A process according to claim 1, wherein the irradiation is carried out at a temperature from 0 to 30° C.

3. A process according to claim 1, wherein the irradiation is effected through quartz glass.

4. A process according to claim 1, wherein after the irradiation, the purified partially fluorinated or perfluorinated hydrocarbon is separated from the irradiated product by distillation.

5. A process according to claim 1, wherein the purified hydrocarbon is selected from the group consisting of 1,1,1,2-tetrafluoroethane, pentafluoroethane, pentafluoropropane, hexafluoropropane, pentafluorobutane, perfluoropropane and perfluorobutane.

6. A process according to claim 1, the at least one impurity comprises an alkene which may be substituted by at least one halogen selected from the group consisting of chlorine and fluorine.

7. A process according to claim 1, wherein the impurity comprises an alkane which is substituted by chlorine and optionally fluorine.

8. A process according to claim 1, wherein an extremely pure, saturated, partially fluorinated or perfluorinated hydrocarbon containing at most 5 ppm of each impurity is prepared.

9. A process according to claim 8, wherein an extremely pure, saturated, partially fluorinated or perfluorinated hydrocarbon containing at most 1 ppm of each impurity is prepared.

10. A mixture of a partially fluorinated or perfluorinated hydrocarbon with 1 to 10 carbon atoms and at least one higher boiling chlorine-containing higher boiling compound, obtained by UV irradiation of a crude product which contains said partially fluorinated or perfluorinated hydrocarbon with 1 to 10 carbon atoms and at least one impurity which absorbs light at $\lambda > 200$ nm, wherein said crude product is irradiated without addition of reactants.

11. A mixture according to claim 10, wherein said at least one impurity is selected from the group consisting of chlorinated alkenes, chlorinated alkanes, chlorofluorinated alkenes and chlorofluorinated alkanes.

* * * * *